US009665940B2

(12) United States Patent
Foelling

(10) Patent No.: US 9,665,940 B2
(45) Date of Patent: May 30, 2017

(54) LIGHT-MICROSCOPY METHOD FOR LOCATING POINT OBJECTS

(71) Applicant: LEICA MICROSYSTEMS CMS GMBH, Wetzlar (DE)

(72) Inventor: Jonas Foelling, Heidelberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 72 days.

(21) Appl. No.: 14/778,638

(22) PCT Filed: Mar. 24, 2014

(86) PCT No.: PCT/EP2014/055800
§ 371 (c)(1),
(2) Date: Sep. 21, 2015

(87) PCT Pub. No.: WO2014/147257
PCT Pub. Date: Sep. 25, 2014

(65) Prior Publication Data
US 2016/0063718 A1  Mar. 3, 2016

(30) Foreign Application Priority Data

Mar. 22, 2013 (DE) .......... 10 2013 102 988

(51) Int. Cl.
*G06K 9/00* (2006.01)
*G06T 7/00* (2017.01)
(Continued)

(52) U.S. Cl.
CPC ....... *G06T 7/0065* (2013.01); *G01N 21/6458* (2013.01); *G02B 3/06* (2013.01);
(Continued)

(58) Field of Classification Search
CPC ..................... G02B 21/0076; G02B 21/16
See application file for complete search history.

(56) References Cited

U.S. PATENT DOCUMENTS 9,179,131 B2 * 11/2015 Foelling ............. H04N 13/0257
2005/0082494 A1 * 4/2005 Motomura ............. G02B 21/16
250/458.1
(Continued)

FOREIGN PATENT DOCUMENTS

DE   102006021317 B3   10/2007
DE   102008024568 A1   12/2009
(Continued)

OTHER PUBLICATIONS

Kao et al ("Tracking of Single Fluorescent Particles in Three Dimensions: Use of Cylindrical Optics to Encode Particle Position", 1994).*

(Continued)

*Primary Examiner* — Avinash Yentrapati
(74) *Attorney, Agent, or Firm* — Leydig, Voit & Mayer, Ltd.

(57) ABSTRACT

A light-microscopy method for locating point objects in a sample arranged in an object space includes imaging the sample onto a detector by an imaging optical unit having a depth of field of predetermined axial extent along an optical axis in the object space, onto which the detector is imaged. The point objects in the sample are located within the depth of field. The first sample image generated by the imaging of the sample onto the detector is evaluated. For locating a respective first point object in a direction of the optical axis, a parameter of a first light spot of one or more light spots of the first sample image representing the first point object is determined, and a rough axial z position related to the first point object is assigned to the parameter based on predetermined association information.

17 Claims, 7 Drawing Sheets

(51) Int. Cl.
| | |
|---|---|
| *G01N 21/64* | (2006.01) |
| *G02B 21/16* | (2006.01) |
| *G02B 21/36* | (2006.01) |
| *G02B 27/58* | (2006.01) |
| *G02B 3/06* | (2006.01) |
| *G02B 21/18* | (2006.01) |
| *G02B 27/00* | (2006.01) |
| *G06K 9/46* | (2006.01) |
| *G06T 7/55* | (2017.01) |

(52) U.S. Cl.
CPC ............ *G02B 21/16* (2013.01); *G02B 21/18* (2013.01); *G02B 21/361* (2013.01); *G02B 21/367* (2013.01); *G02B 27/0075* (2013.01); *G02B 27/58* (2013.01); *G06K 9/4671* (2013.01); *G06T 7/55* (2017.01); *G06T 2207/10028* (2013.01); *G06T 2207/10056* (2013.01); *G06T 2207/30004* (2013.01); *G06T 2207/30204* (2013.01)

(56) References Cited

U.S. PATENT DOCUMENTS

| | | | |
|---|---|---|---|
| 2009/0134342 A1* | 5/2009 | Hell | G01N 21/6428 250/459.1 |
| 2010/0278400 A1* | 11/2010 | Piestun | G01N 21/6456 382/128 |
| 2010/0321484 A1* | 12/2010 | Kishima | G02B 21/365 348/79 |
| 2011/0160083 A1* | 6/2011 | Hell | G01N 21/6428 506/9 |
| 2011/0249866 A1* | 10/2011 | Piestun | G06T 7/77 382/103 |
| 2012/0300293 A1 | 11/2012 | Selvin et al. | |
| 2013/0119273 A1* | 5/2013 | Foelling | G02B 21/06 250/459.1 |
| 2013/0229494 A1* | 9/2013 | Dyba | G02B 21/367 348/47 |
| 2015/0192510 A1* | 7/2015 | Piestun | G01B 11/002 702/151 |

FOREIGN PATENT DOCUMENTS

| | | |
|---|---|---|
| DE | 102011053232 A1 | 3/2013 |
| WO | WO 2006127692 A2 | 11/2006 |
| WO | WO 2007128434 A1 | 11/2007 |
| WO | WO 2008091296 A2 | 7/2008 |
| WO | WO 2009085218 A1 | 7/2009 |

OTHER PUBLICATIONS

Spiedel et al. ("Three-dimensional tracking of fluorescent nanoparticles with subnanometer precision by use of off-focus imaging", 2003).*

Toprak et al ("Three-Dimensional Particle Tracking via Bifocal Imaging", 2007).*

Kao H P et al: "Tracking of Single Florescent Particles in Three Dimensions: Use of Cylindrical Optics to Encode Particle Position", Biophyisical Journal, Cell Press, US, vol. 67, No. 3, Sep. 1, 1994 (Sep. 1, 1994), pp. 1291-1300, XP002523344.

Laurent Holtzer, et al., Nanometric three-dimensional tracking of individual quantum dots in cells, Applied Physics Letters 90, 053902, Feb. 1, 2007, pp. 1-3.

Erdal Toprak, et al., "Three-Dimensional Particle Tracking via Bifocal Imaging", Nano Letters, vol. 7, No. 7, Jun. 6, 2007, pp. 2043-2045.

Bo Huang, et al., "Three-Dimensional Super-Resolution Imaging by Stochastic Optical Reconstruction Microscopy", Science 319, 810, Feb. 8, 2008, pp. 809-813.

Manuel F Juette, et al., "Three-dimensional sub-100 nm resolution fluorescence microscopy of thick samples", Nature Methods, Advance Online Publication, May 11, 2008, pp. 1-3.

Sri Rama Prasanna Pavani, et al., "Three-dimensional, single-molecule fluorescence imaging beyond the diffraction limit by using a double-helix point spread function", PNAS, vol. 106, No. 9, Mar. 3, 2009, pp. 2995-2999.

Michael J. Rust, et al., Sub-diffraction-limit imaging by stochastic optical reconstruction microscopy (STORM), Nature Method, vol. 3, No. 10, Oct. 2006, pp. 793-795.

C. Geisler, et al., Resolution of λ/10 in fluorescence microscopy using fast single molecule photo-switching, Appl. Phys. A 88, Jun. 1, 2007, pp. 223-226.

* cited by examiner

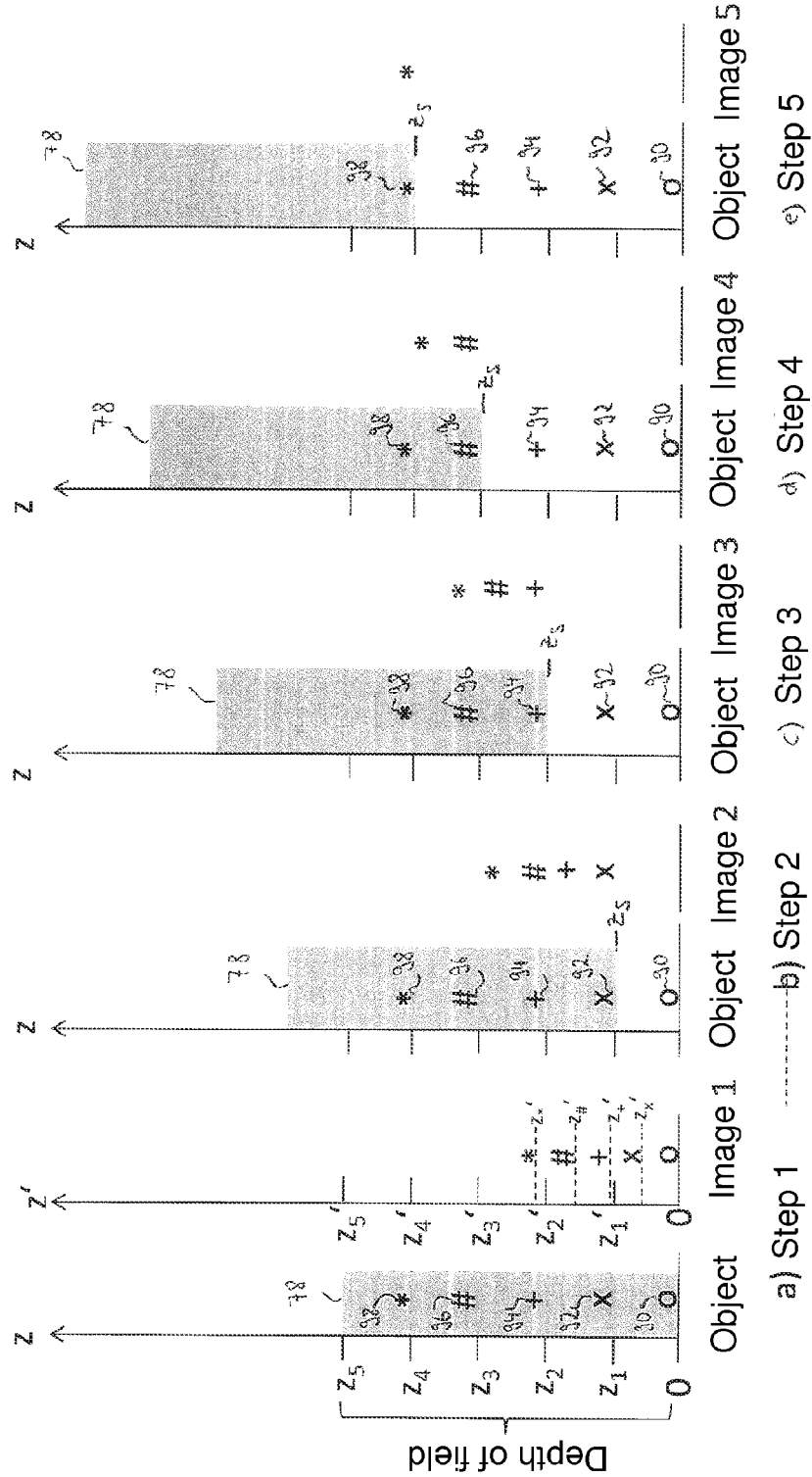

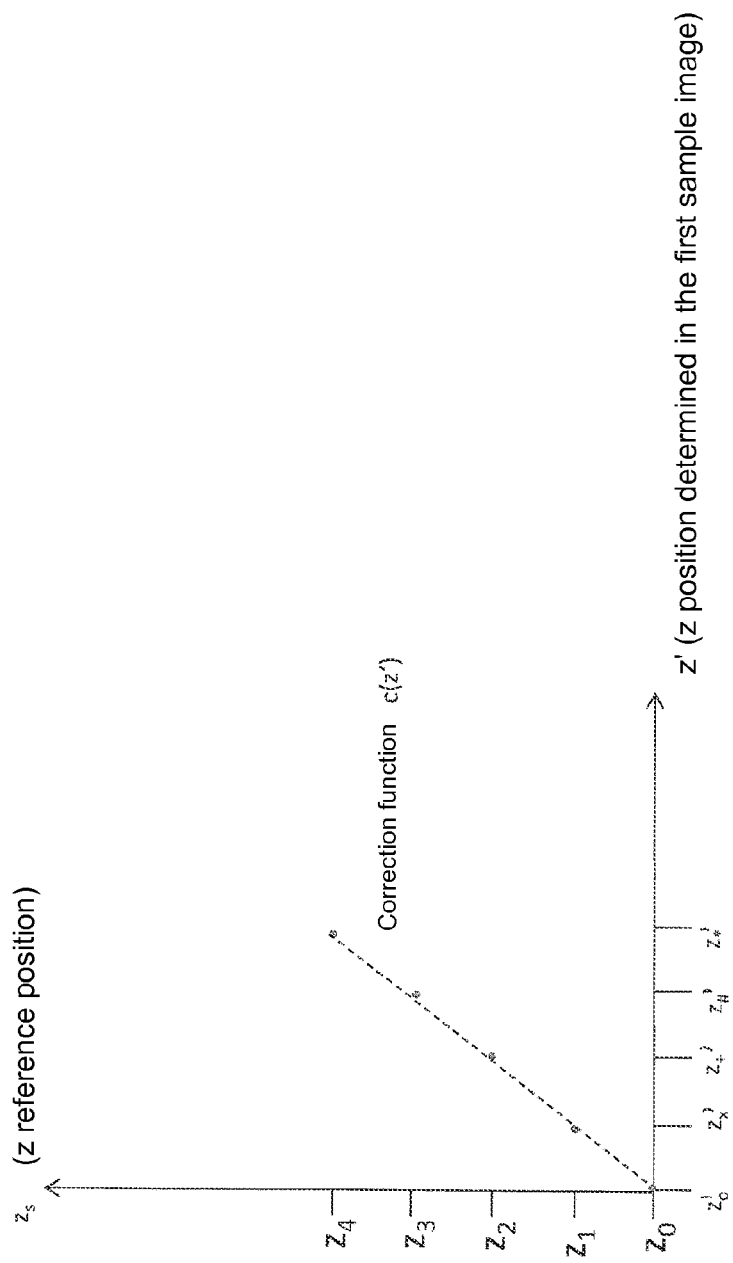

LIGHT-MICROSCOPY METHOD FOR LOCATING POINT OBJECTS

CROSS REFERENCE TO RELATED APPLICATIONS

This application is a U.S. National Stage Application under 35 U.S.C. §371 of International Application No. PCT/EP2014/055800 filed on Mar. 24, 2014, and claims benefit to German Patent Application No. DE 10 2013 102 988.4 filed on Mar. 22, 2013. The International Application was published in German on Sep. 25, 2014 as WO 2014/147257 A1 under PCT Article 21(2).

FIELD

The invention relates to a light-microscopy method for locating point objects in a sample, wherein the sample arranged in an object space is imaged onto a detector.

BACKGROUND

Light-microscopy imaging methods have been developed, with which, based on a sequential locating of individual markers, particularly fluorescent molecules, sample structures can be represented, which are smaller than the diffractive resolution limit of conventional light microscopes. Such methods are for example described in WO 2006/127692 A2; DE 10 2006 021 317 B3; WO 2007/128434 A1, US 2009/0134342 A1; DE 10 2008 024 568 A1; WO 2008/091296 A2; "sub-diffraction-limit imaging by Stochastic optical reconstruction microscopy (STORM)," Nature Methods 3, 793-796 (2006), M J Rust, M. Bates, X. Zhuang; "Resolution of Lambda/10 in fluorescence microscopy using fast single molecule photo-switching", Geisler C. et al, Appl. Phys. A, 88, 223-226 (2007). This new branch of microscopy is also referred to as locating microscopy. The methods used are known in the literature e.g. under the names (F) PALM ((Fluorescence) Photoactivation Localization Microscopy), PALMIRA (PALM with Independently Running Acquisition), GSD (IM) (Ground State Depletion Individual Molecule Return) Microscopy) or (F) STORM ((Fluorescence) Stochastic Optical Reconstruction Microscopy).

The new methods have in common that the sample structures to be imaged are prepared with point objects, so-called markers, which have two distinctive states, namely a "bright" state and a "dark" state. For example, when fluorescent dyes are used as markers, the bright state is a fluorescence-capable state and the dark state is a not fluorescence-capable state.

In preferred embodiments, as e.g. in WO 2008/091296 A2 and WO 2006/127692 A2, photoswitchable or photoactivatable fluorescent molecules are used. Alternatively, as e.g. in DE 10 2006 021 317 B3, inherent dark states of standard fluorescent molecules can be used.

For imaging sample structures with a resolution that is higher than the conventional resolution limit of the imaging optical unit, a small partial amount of the markers is now repeatedly transferred to the bright state. Thereby, the density of the markers forming this active partial amount is to be selected so that the average distance of adjacent markers in the bright and hence in the light-microscopy imaging state is greater than the resolution limit of the imaging optical unit. The markers forming the active partial amount are imaged onto a spatially resolving light detector, e.g. a CCD camera, so that a light distribution in the form of a light spot is detected, whose size is determined by the resolution limit of the optical unit.

In this manner, a large number of raw data individual images is recorded, in which respectively another active partial amount is imaged. The focus positions of the light distributions are then determined in an image evaluation process, which represent the punctiform markers in the bright state. The focus positions of the light distributions determined from the raw data individual images are then compiled in an overall presentation in the form of an overall image data set. The high-resolution overall image resulting from this overall presentation reflects the distribution of the markers.

For a representative reproduction of the sample structure to be imaged, a sufficient number of marker signals have to be detected. However, since the number of markers in the respectively active partial amount is limited by the minimum average distance, which two markers must have in the bright state, a lot of raw data individual images have to be recorded in order to image the sample structure completely. Typically, the number of raw data individual images is in a range from 10,000 to 100,000.

In addition to the above-described lateral position determination of the markers in the object plane (hereinafter also referred to as x-y-plane), a position determination in the axial direction (hereinafter also referred to as z direction) can also take place. The axial direction is thereby meant to be the direction in the optical axis of the imaging optical unit, thus the main propagation direction of light.

Three-dimensional locations are known from so-called "Particle-Tracking" experiments, as described in Kajo et al, 1994, Biophysical Journal, 67, Holtzer et al, 2007 Applied Physics Letters, 90, and Toprak et al, 2007, Nano Letters, 7 (7). They have also already been used in imaging methods based on the above-described switching and locating of individual molecules. For this purpose, Huang et al, 2008, Science, 319 and Juette et al, 2008, Nature Methods, are referred to. For the state of the art, Pavani et al., 2009, PNAS, 106, is further referred to.

A locating of a punctiform object in the z direction can in principle take place in that the change of a light spot detected on the detection surface of the camera is evaluated, which is visible when the point object moves from the optically conjugated sharpness or focal plane to the detection surface. Thereby, a point object is to be understood in the following an object whose dimensions are smaller than the diffractive resolution limit of the imaging optical unit, in particular of the detection objective. In this case, the detection objective images such an object in the form of a three-dimensional focus light distribution into the image space. The focus light distribution generates a light spot on the detection surface of the camera, which light spot is characterized by the so-called "point spread function", that is, point-imaging function or PSF in short. If the point object is now moved in the z direction by the focus, that is, perpendicular to the focus plane, the size and the form of the PSF change. If the detection signal corresponding to the detected light spot with respect to the size and the form of the PSF is analyzed, conclusions with regard to the actual z position of the object can thus be obtained.

If the point object is located too far from the focal plane, the light spot generated on the detection surface of the camera is so blurred that the corresponding measurement signal within the conventional measurement noise is no longer perceptible. Thus, there is a region in the object space in the z direction around the central focal or focal plane, within which a point object on the detection surface generates a light spot, which is still sharp enough to be able to be evaluated for the locating of the point object in the z direction. This region containing the focal plane in the z direction is hereinafter referred to as "depth of field".

With a three-dimensional locating, however, the fundamental problem exists that the PSF derived from a point object is symmetrical with respect to the detection surface. This means that the PSF indeed changes when the point object is moved out from the focal plane, so that the distance of the point object to the focal plane can be determined. However, the change of the PSF is symmetrical on both sides of the focal plane, so that it cannot be decided on which side of the focal plane the point object is present within the depth of field.

There are known various methods how to deal with the above-described problem. Examples are methods which are referred to in professional circles as "astigmatism" (the above-mentioned documents Kajo et al., Holtzer et al. and Huang et al.), "Bi-plane method" (see Toprak et al. and Juette et al.) and "Double helix method" (see Pavani et al.). These methods have in common that, for locating the point object in the z direction, the light spot generated on a detector for determining a parameter is analyzed and that a z position of the point object is assigned to this parameter. This association takes place by means of an association information determined in advance, which relates the parameter to the z position of the point object. For example, a magnitude characterizing the form of the light spot is considered as the parameter, as in the astigmatism method, or, as in the case of the bi-plane method, a magnitude which relates the extents of two light spots to each other, which originate from one and the same light spot and detection surfaces are generated, whose associated focal planes are offset to each other in the object space in the z direction.

A problem is now that the association information enabling an association between the parameter determined in the measurement and an axial z position determined in advance of the actual measurement is often so inaccurate that a precise determination of the z-position is not possible. The association information is thus dependent on changes in the optical properties of the sample.

Even small changes in the optical properties result in imaging errors with the high performance optics required in the localization microscopy, e.g. spherical aberrations. This has the consequence that the form of the PSF given by the light spot changes and thus the determined association information determined for example in the form of a calibration curve is no longer correct for the new optical conditions. In this case, the wrong z position is assigned to the light spot detected on the detector.

For the user, it is often difficult to introduce calibration elements as e.g. fluorescent beads into a biological sample, which shall be measured ultimately, by means of which beads the above-mentioned calibration curve can be prepared. This is especially valid when these calibration elements shall fluoresce in different colors, in order to avoid errors by the chromatic aberration.

Therefore, a preferred variant in practice is to carry out the calibration, that is, the determination of the association information, with an own calibration sample. Here, however, the problem of erroneous calibration has a particularly strong effect, as the optical properties of the calibration sample are never identical to the actual measurement sample. Small differences in the thickness of the cover glass or differences in the embedding medium of the sample can already lead to a significant deviation of the form of the calibration curve.

Even when calibration samples were introduced directly into the sample to be measured with a great experimental effort, the calibration curve determined in this manner can be faulty. For example, even small temperature changes lead to the fact that typical immersion oils change their refractive index, which in turn leads to spherical aberrations in the image.

Thus, a change in the calibration curve between the date of commencement of the calibration and the time of actual measurement may also occur in one and the same sample. In addition, the signal of a fluorescent bead used as a calibration sample certain size differs always from the signal of the point object forming single molecule, which in turn leads to an erroneous calibration.

In practice, these problems lead to the fact that accurate absolute determinations of the z position of a point object are often not possible. It is thus although quite possible to determine relative differences in the z position and thus also to separate and adjacent structures with high resolution from one another. However, a statement of how far any adjacent structures are removed from one other exactly, is difficult. It is thereby important to distinguish between the resolution, that is, the possibility to separate closely spaced structures from each other, and the absolute position determination. The association information used in the state of the art thus regularly allows for example the desired resolution in the form of a calibration curve, but not a precise determination of the absolute z position of the point object. This fact can also be described as a substantial (typically nonlinear) distortion of the three-dimensional image in the z direction, which results from the optical aberrations. Especially in modern biology, this is a big problem. For example, the exact form and arrangement of proteins influence their function dramatically. In order to obtain information regarding the structural arrangement, one is thus dependent on accurate and absolute measurements in all three spatial directions. The insufficient calibration options that exist in the state of the art for the locating in the z direction do not allow sufficient reliability.

SUMMARY

In an embodiment, a light-microscopy method for locating point objects in a sample arranged in an object space is provided. The sample is imaged onto a detector by an imaging optical unit having a depth of field of predetermined axial extent along an optical axis in the object space, onto which the detector is imaged. The point objects in the sample are located within the depth of field. The first sample image generated by the imaging of the sample onto the detector is evaluated. For locating a respective first point object in a direction of the optical axis, a parameter of a first light spot of one or more light spots of the first sample image representing the first point object is determined, and a first axial z position related to the first point object is assigned to the parameter based on predetermined association information. The method includes shifting the depth of field within which the point objects are located in the object space relative to the sample along the optical axis by a predetermined axial displacement, the predetermined axial displacement being smaller than the predetermined axial extent of the depth of field; imaging, by the imaging optical unit, the sample onto the detector with the axially shifted depth of field to generate at least a second sample image; determining second image z positions of the point objects in the second sample image based on the predetermined axial displacement; comparing first image z positions of the point objects in the first sample image to the second image z positions of the point objects in the second sample image; and generating, based on the comparing the first image z positions of the point objects in the first sample image to the second image z positions of the point objects in the second sample image, correction information as to correct the first axial z position related to the first point object based on the predetermined association information.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 6 is a schematic representation for illustrating how the z positions of the point objects are corrected by the shift of the depth of field according to an embodiment of the invention; and FIG. 7 is a graphical representation which shows an example correction function generated by the method according to FIG. 6.

DETAILED DESCRIPTION

Figure 1:
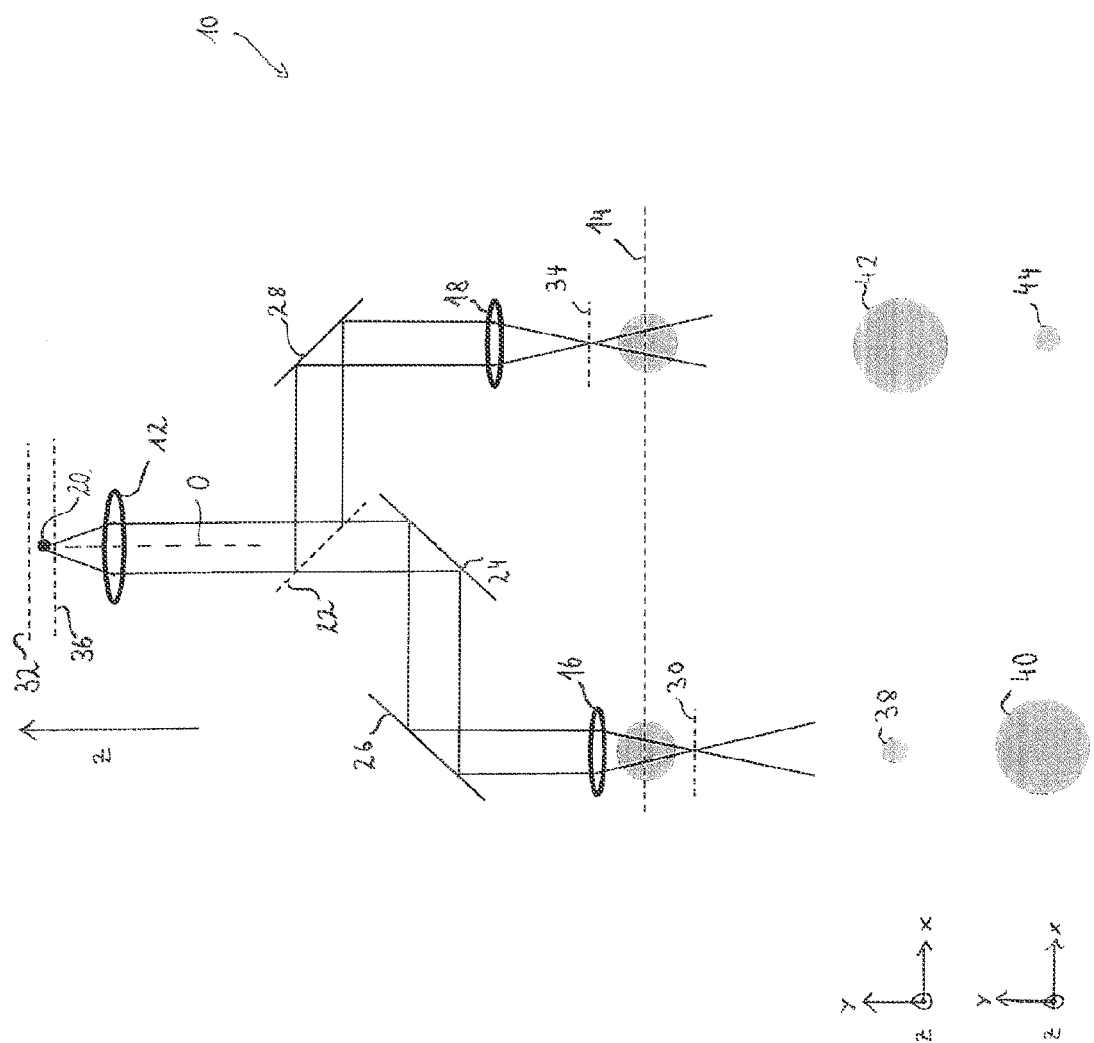
FIG. 1 is a schematic representation showing an embodiment for locating a point object in the z-direction.

In an embodiment, the invention provides a light-microscopy method for locating point objects of the above-mentioned type in such a manner that the point objects can be located more precisely than previously in the z direction.

In an embodiment, the invention relates to a light-microscopy method for locating point objects in a sample, wherein the sample arranged in an object space is imaged onto a detector by means of an imaging optical unit having a depth of field of a predetermined axial length along its optical axis in the optical space, and the point objects contained in the sample are localized within the depth of field, in that a first sample image generated by the imaging of the sample on the detector is evaluated, wherein, for locating the respective point object in the direction of the optical axis, a parameter of a light spot of the first sample image representing the point object is determined and an axial z position related to the point object is assigned to this parameter in dependence on a predetermined association information.

In an embodiment, the depth of field, in which the point objects are located, is shifted in the object space relative to the sample along the optical axis by a predetermined axial displacement, which is smaller than the axial extension of the depth of field; the sample is again imaged onto the detector with the axially shifted depth of field by means of the imaging optical unit and at least one second sample image is generated; the z positions of the point objects are determined in the second sample image in dependence on the predetermined axial displacement; the z positions of point objects determined in the first sample image are compared to the z positions determined in the second sample image; and a correction information is generated in dependence on this comparison, by means of which the z positions of the point objects determined in dependence on the association information are corrected.

As already mentioned above, the depth of field in the object space according to an embodiment of the invention is to be understood as a region in the z direction about the central focal or focal plane, in which a point object generates a light spot on the detector, which is still sharp enough to be able to be evaluated for locating the point object in the z direction. It is thereby not necessary to make full use of the maximum possible depth of field. It can thus be sensible to deliberately reduce the depth of field in dependence on the desired locating accuracy and thereby exclude quite blurry but still evaluable light spots from the evaluation.

A solution according to an embodiment of the invention provides for correcting a faulty association information due to optical imaging errors, which is, e.g., present in the form of a stored calibration function, during the measurement. For this, the depth of field of the imaging optical unit whose axial extent along the optical axis is known, is shifted relative to the sample by an axial displacement, which is smaller than the axial extension of the depth of field. In other words, the shift takes place in such a manner that there is some overlap along the optical axis between the original depth of field and the shifted depth of field in the object space.

This overlap is achieved in that the axial displacement, by which the depth of field is moved along the optical axis, is smaller than the axial extension of the depth of field. The displacement is thus for example in a range from 5 to 90%, 10 to 80%, 15 to 70%, 20 to 60% or 25 to 50% of the axial extension of the depth of field. It goes without saying that these ranges are only meant to be exemplary.

The shift of the depth of field according to an embodiment of the invention by an axial displacement, which is smaller than the axial extension of the depth of field is to be understood that the two considered depth of fields, namely, the original and the shifted depth of field, have an overlap along the optical axis. This means that the invention also covers a sequence of steps of shifts of the depth of field, where the depth of field is shifted by a displacement which is larger than the extension of the depth of field in a single step, provided that the sequence of steps altogether leads to the above-mentioned axial overlap being realized between the considered depth of fields.

The fact that the axial displacement by which the depth of field will be moved to one or more steps in the object space is smaller than the axial extension of the depth of field, means that shifting of the depth of field in the z direction takes place with an accuracy, which exceeds the resolution accuracy of the imaging optical unit in the z direction. This can for example be achieved via a piezoelectric actuator which shifts either the imaging optical unit or the sample in the z direction.

Likewise, it is possible to use a suitable optical element, e.g. a deformable lens, a deformable or movable mirror or a spatial light modulator for shifting the depth of field.

The correction according to an embodiment of the invention enables a three-dimensional microscopic imaging beyond the depth of field, which was not possible previously without further ado due to the distortion of the image in the z direction. Although it is in principle already conceivable in conventional methods, after recording an image, to move the image in the z direction exactly by an amount which corresponds to the axial extension of the depth of field, and then to record another image, to finally join these two images in the z direction. From this, an overall image would result, which extends in the z direction over two depth of fields. However, this procedure requires a locating of point objects in the z direction with a precision that was not previously given. The precision achieved by a method according to an embodiment of the invention allows a joining of several images in the z direction, without falsifying superimpositions or gaps occurring between images.

If the correction information by means of which the z positions of the point objects are corrected are provided in the form of a correction rule, by means of which the z positions of the point objects determined with the original (faulty) association information for positions of point objects are assigned corrected z positions according to an embodiment of the invention, for each of the successive depth of fields in the z direction an own correction rule is possibly determined in the above-described case and used for locating the point objects in this depth of field.

A method according to an embodiment of the invention can particularly be used profitably in such cases, in which the calibration curve is variable by changing the optical properties of the sample or of the light path through the sample. Thus, different calibrations can be valid for different regions of the sample. An example for this are samples embedded in aqueous media. The deeper the focal plane is brought into the sample, the more water the light has to pass through, which has a different refractive index than the other optical materials such as immersion oil and glass. Thus, the optical imaging and hence also the calibration curve changes in dependence on the z position of the depth of field.

According to an embodiment of the invention, the first or second sample image is respectively meant to be an image data set, as is for example realized by the raw data individual image(s) explained above.

Preferably, at least one z difference position is defined within the depth of field along the optical axis, which is stationary relative to the depth of field. At least one of the light spots from the at least one second sample image generated on the detector with an axially shifted depth of field, which represent the point objects arranged in the axially shifted depth of field in the z direction are defined as reference light spot. The z position of the point object, which is represented by the reference light spot is determined in the object space in dependence on the axial displacement of the depth of field and the z reference position. One of the light spots, from the first sample image, which represents the same point object as the reference light spot of the second sample image is identified as a comparison light spot. In dependence on a deviation of the z position of the point object, which is represented by the comparison light spot, with respect to the z position of the same point object, which is represented by the reference light spot, the correction information is generated, by means of which z positions of the point objects determined in dependence on the association information are corrected.

Thus, at least one z reference position is defined within the depth of field, which is stationary relative to the depth of field. The latter means that the z reference position is moved so to speak with the depth of field in the object space. The axially upper or the axially lower limit of the depth of field in the object space can for example be defined as z reference position. The z position in which the central focal plane of the depth of field is present, is also suitable as z reference position. Furthermore, it is possible to define not only one but several reference positions within the depth of field, whose positions in the object space are known, and which make it possible, therefore, to determine the z positions of those point objects, which are in the z reference positions, in a faultless manner.

This embodiment thus provides to use the precise shifting of the depth of field, which is possible unaffected by optical imaging errors, in order to carry out reference measurements in the sample during the current measurement e.g. at certain intervals, by means of which an erroneous calibration can be corrected. This correction is based on that, in the sample image, which is recorded with an axially shifted depth of field, those point objects that are located within the shifted depth of field in the z-reference positions, can be determined without error, because the z reference positions are known. With the knowledge of these correct z positions, a correction information can be generated according to an embodiment of the invention, which can then be used to correct the z positions of the point objects determined in this sample image in a sample image recorded prior to the shifting of the depth of field. When the correction information is gradually completed by successively shifting the depth of field, a distortion of the overall image caused by a wrong calibration can be corrected in this way.

Preferably, the depth of field is axially shifted in several steps. In each of these steps, the correction information is then generated by means of the respective reference light spot and the respective comparison light spot. The z positions of the point object determined in dependence on the association information are finally corrected by means of the gradually generated correction information. By the gradually shifting of the depth of field, the original, that is, unshifted depth of field, is scanned with the z reference position. As the z reference position in each step is known, the point objects, which are identified in the z positions coinciding with the respectively shifted z reference position within the original depth of field, can be located exactly.

Based on these exactly determined z positions, the z positions lying between these positions within the original depth of field can then also be determined by means of the correction information.

The z position determined in dependence on the association information for the respective comparison light spot is preferably replaced in each step by the z position determined for the corresponding reference light spot, and, by this replacement, a correction function forming the correction information is generated. This correction function thereby preferably covers the entire depth of field, with which the first sample image has been recorded.

In a preferred embodiment, intermediate values of the correction function, for which no comparison light spots and reference light spots are available by the gradual shifting of the depth of field, are determined by interpolation. The z-positions, which are determined exactly by shifting the z reference position, thereby form support locations, on the basis of which the interpolation, for example a simple spline interpolation, can be carried out. For example, a suitable model function is selected, which takes typical calibration errors into account, and this model function is adapted to the support locations mentioned above, in order to obtain the desired correction function.

Preferably, the z positions of the point objects determined by gradually shifting the depth of field are superimposed to a total localization image. Accordingly, the (second) sample images are not only used for correcting the z positions determined in the original (first) sample image, but to build a total localization image which extends in the z direction over a region which is larger than the original depth of field.

Preferably, the axial displacement by which the depth of field will be shifted in the object space is detected by a sensor. This ensures that the axial displacement which enters the correction of the determined z positions of the point objects is always known precisely. The shifting of the depth of field relative to the sample can take place in that either the sample is moved relative to the imaging optical unit or the imaging optical unit relative to the sample along the optical axis. However, the invention is not restricted to this. It is thus for example also possible to use a deformable lens, a deformable mirror, a spatial light modulator or the like, in order to shift the depth of field in the object space along the optical axis of the imaging optical unit.

In an embodiment, a cylindrical lens upstream of the detector is used, which leads to a distinguishable change of the form of the light spot generated on the detector, when the point object assigned to the light spot is moved along the optical axis from one side to the other side of a focal plane lying in the depth of field. The change of the form of the light spot can then be used as a parameter for locating in the z direction.

At this point it should be noted that the term "form of the light spot" can be understood according to the invention that it refers not only on the form of a single light spot, but also includes the form of an entirety formed by several light spots, as can for example be found in the double helix method mentioned at the outset. There, for example, two light spots are considered which carry out a rotational movement to each other.

Preferably, the comparison structure formed by the reference light spots is identified in consideration of their brightness, that is, in consideration of the total number of individual spots that contribute to this structure. This embodiment is particularly advantageous when the z positions determined with the shifted depth of field are not only used for the correction of z positions determined previously by means of the association information, but also for the generation of a total localization image. Interfering brightness differences in the total localization image are avoided by this further development.

The association information can for example be obtained in that a calibration point object within the depth of field is moved along the optical axis and the parameter of a light spot representing the calibration point object of a calibration image generated on the detector in dependence on the z position of the calibration point object is detected. The form shape and/or the expansion of the light spot on the detector is for example used as the parameter.

Figure 2:
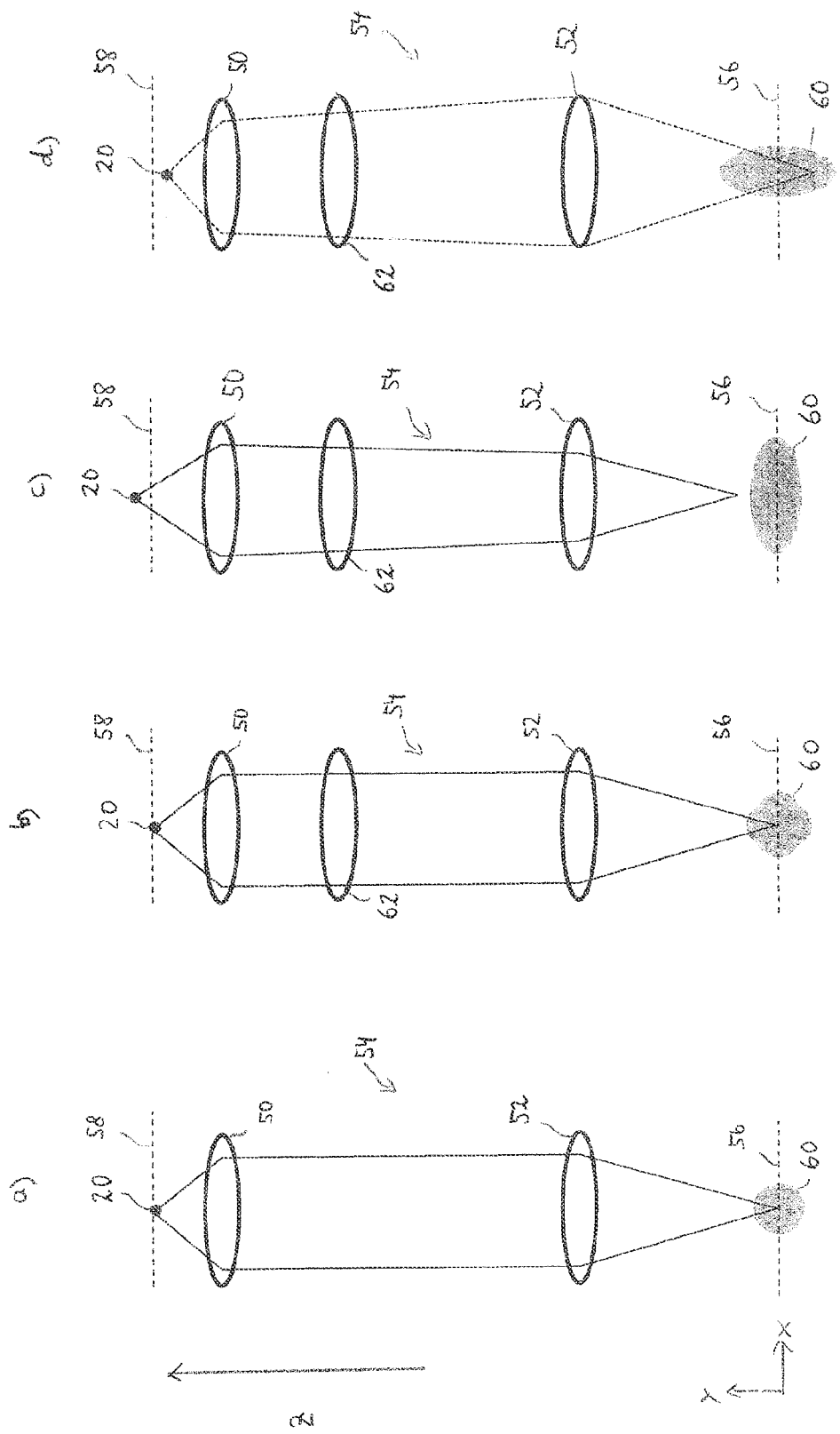
FIG. 2 is a schematic representation showing an alternative embodiment for locating a point object in the z-direction.
Figure 3:
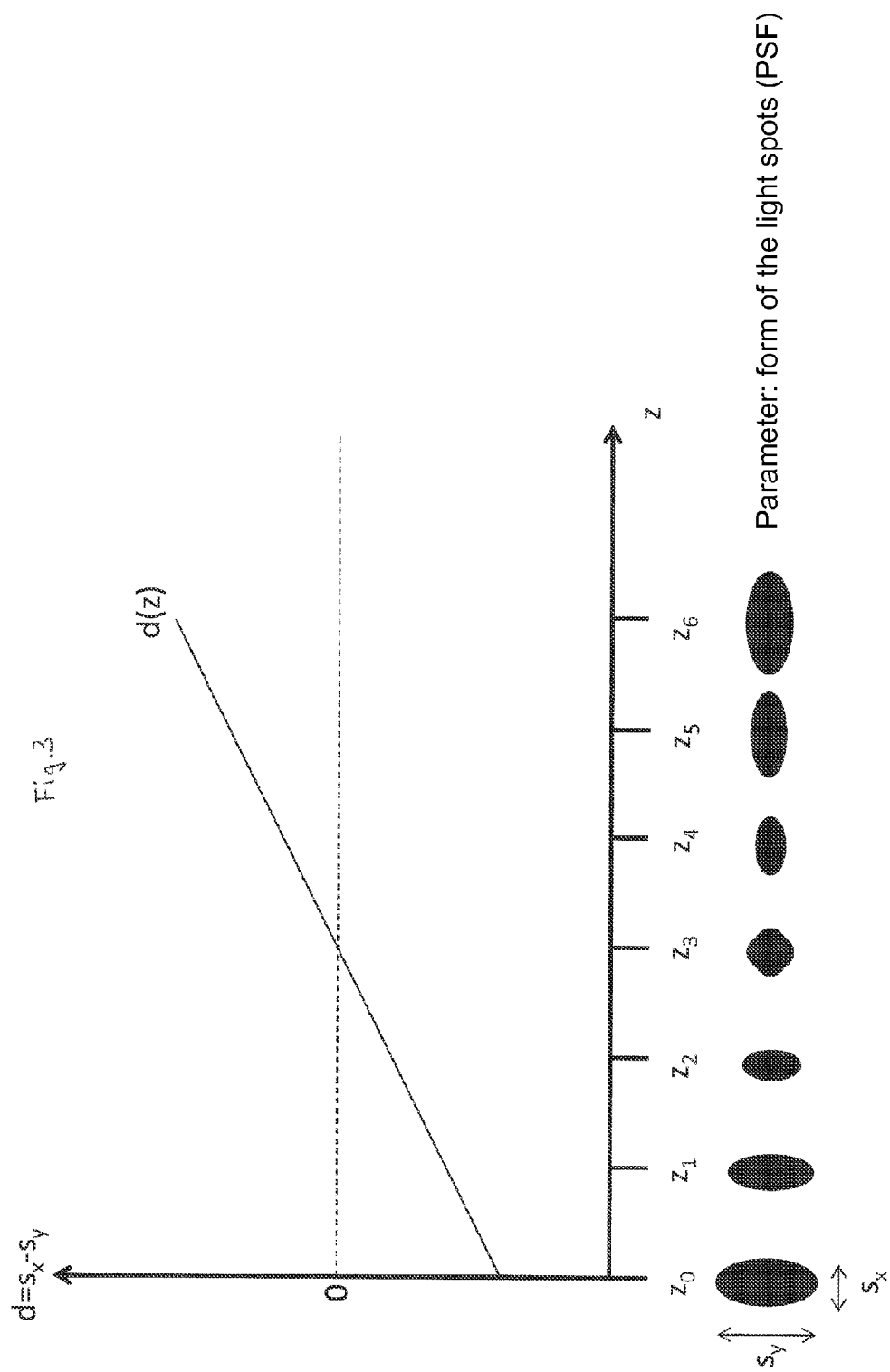
FIG. 3 is an association rule, by which the form of a light spot detected on a detection surface with respect to the z position of a point object is set relative to a focal plane, according to an embodiment of the invention.

First, referring to FIGS. 1 to 3, two embodiments are explained, in which a parameter is determined in a different manner, which allows a locating of point objects in the z direction.

FIG. 1 shows a light-microscopy device 10 with an objective 12 as imaging optical unit and a detection surface 14. The arrangement according to FIG. 1 has two separate detection channels, of which a left channel in FIG. 1 is substantially given through the objective 12 and a first tube lens 16, while a right channel in FIG. 1 is formed of the objective 12 and a second tube lens 18.

The light originating from a point object 20 is guided through a beam splitter 22 and deflecting mirrors 24, 26 and 28 into the two detection channels in equal parts.

The two detection channels differ slightly in their focal position. This means that the first detection channel has a first image plane 30, which is optically conjugated to a first focal plane 32, while the other detection channel has a second image plane 34 offset compared to the first image plane 30 in a direction parallel to the optical axis O of the objective 12, that is, in the z direction, which is optically conjugated to a second focal plane 36, which is again offset in the z direction compared to the first focal plane is 32.

When the point object 20 to be located is in the focal plane of a detection channel, it is imaged there sharply by the objective 12, while it is imaged blurry in the other detection channel. When it is between the two focal planes 32 and 36, it is imaged blurry in both detection channels.

In FIG. 1, the above-described fact is illustrated by light spots 38, 40, 42 and 44, which are generated on the detection surface 14 in dependence on the z position of the point object 20 relative to the focal planes 32 and 36. The light spots 38, 40, 42, 44 are therefore shown in the plan view of the x-y plane in FIG. 1. The light spots 38, 40, 42 and 44 are respectively characterized by the PSF, which results from the focus light distribution generated by the objective 12 on the detection surface 14.

If the point object 20 is in the first focal plane 32, the comparatively small light spot 38 results on the detection area 14 in the left detection channel and in the right detection channel the large light spot 42 compared to it. If, however, the point object 20 is located in the focal plane 36, the large light spot 40 results on the detection surface 14 in the left detection channel, the small light spot 44 in the right detection channel.

From the light spots 38, 40, 42, 44 generated on the detection surface 44, a parameter can now be derived, which is a measure for the z position of the point object 20 relative to the focal planes 32 and 36. For example, as a parameter, the expansion of the light spot 38 or 44 generated in the left detection channel can be put into proportion with the expansion of the light spot 42 or 44 generated in the right detection channel.

FIG. 2 shows an embodiment in which the above-mentioned parameter, which enables the determination of the z position of the point object is detected in another manner. FIG. 2 thereby shows in the partial image a) firstly a conventional arrangement in which the point object 20 is imaged onto a detection surface 56 via an imagining optics 54 formed by an objective lens 50 and a tube lens 52. The point object 20 shall thereby be located in a focal plane 58, which is an optically conjugated surface to the detection surface 56.

The imaging optical unit 54 forms the light originating from the point object 20 into a three-dimensional focus light distribution, which falls onto the detection surface 56. The detection surface 56 detects a light spot 60 in such a manner, which represents a planar section through the focus light distribution perpendicular to the z direction. In order to illustrate the matter better, the light spot 60 is represented in plan view on the detection surface 56, that is, in the x-y plane in FIG. 2.

In the case represented in the partial image a) of FIG. 2, where the point object 20 is located in the focal plane 58, the light spot 60 has a circular form on the detection surface 56, that is, a form which is symmetrical with regard to reflections at the x-z plane and the y-z plane.

FIG. 2 shows an inventively modified embodiment in partial image b), where a cylindrical lens 62 is provided in addition to the object 50 and the tube lens 52. The cylindrical lens 62 has different refractive powers in the x- and y-direction and thus different focus positions in the x- and y-direction. Accordingly, the light spot 60 on the detection surface 56 is deformed in a cross-shaped manner in the x- and y-direction. The point object 20 is located in the partial image b) exactly in the middle of two different focal planes, wherein this center position is again designated as 58. However, the cross-shaped light spot 60 remains symmetrical in the sense specified above.

FIG. 2 shows a case in the partial image c) in which the point object 20 is arranged above the focal plane 58. This offset from the focal plane 58 causes that the light spot 60 on the detection surface 56 is deformed asymmetrically to an ellipse. The elliptical shape of the light spot 60 thereby becomes more pronounced the farther the point object 20 departs from the focal plane 58.

FIG. 2 shows a case in the partial image d) in which the point object 20 is located below the focal plane 58. Here, too, the light spot 60 is deformed elliptically on the detection surface 56, but in an orientation which is different from the orientation of the light spot 60 in the partial image c). Accordingly, it can be recognized by means of the form of light spot 60 whether the point object 20 is arranged above or below the focal plane 40. As can be seen from the representations of FIG. 2, the z position of the point object 20 relative to the focal plane 58 can be determined by the form and the extent of the light spot 60 on the detection surface 56. This takes place by means of an association rule in the present embodiment, which is represented in an exemplary manner in FIG. 3. Such an association rule can be obtained by calibration measurements, in which a calibration point object moves in the z direction from one side to the other side of the focal plane 58, and thereby the form of the light spot is determined for the z positions which are now known. An association rule is obtained thereby, which makes it possible in the subsequent measurement to associate the correct z position with the measured light spot. In practice, a special calibration sample is used for this, e.g. a sample with fluorescent beads or illuminated and straying nanoparticles as calibration point objects.

FIG. 3 shows an association rule created according to the above implementations. There, the difference of the extent of the light spot in the x direction designated with $s_x$ and the extent of the light spot PSF in the y direction designated with $s_y$ is defined as the parameter. Thus, an association rule d (z) results, which makes it possible to determine a z position for each measured light spot in the actual image recording. This position is then stored together with the x-y position and is available for the generation of a high-resolution three-dimensional image. The determination of an association rule, by means of which the z positions of the point objects can be detected is not limited to the embodiments explained above. Thus, the above-mentioned double helix method is for example also suitable to generate such an association rule.

In addition, it should be noted that an association rule in the functional form of the type shown in FIG. 3 is only an exemplary embodiment. Thus it is e.g. also possible to carry out image comparisons in the form of correlations between the measured PSFs and the previously stored or calculated PSFs. The z position of the stored or calculated PSF, which has the greatest similarity to the measured PSF, is then considered as the correct z position. If a measured PSF is not identical to one of the stored or calculated PSFs with regard to its form, a z position can thus be assigned to for example by interpolation, which lies between the z positions of the stored or calculated PSFs, that are most similar to the measured PSF.

With reference to FIGS. 4-7, it is explained following in an exemplary manner how the location of point objects based on an association rule of the type described above species can be corrected according to embodiments of the invention.

Figure 4:
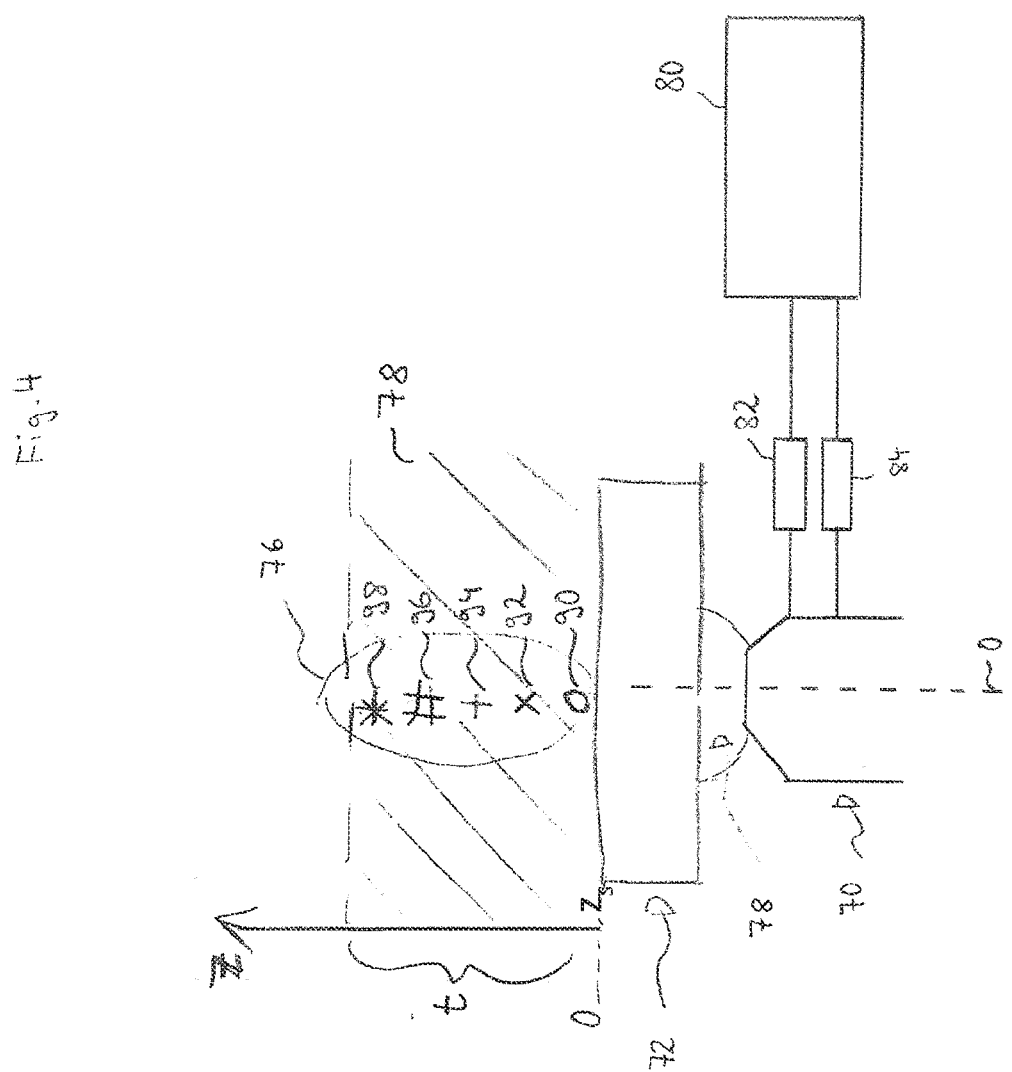
FIG. 4 is a schematic representation in which the depth of field used according to an embodiment of the invention is illustrated.

FIG. 4 shows an embodiment of the microscopic device according to an embodiment of the invention in a purely schematic representation, wherein only those components are indicated in FIG. 4 which serve for the explanation of the correction method according to an embodiment of the invention. In particular, the detector is omitted in FIG. 4.

In the arrangement according to FIG. 4, an objective 70 images a sample 76 mounted on a cover glass 72 through an immersion medium 78 onto the detector. The objective 70 has a depth of field 78, which has an axial extent t along the optical axis O of the objective 70, that is, in the z direction. The depth of field 78 is defined in such a manner that point objects located within the depth of field 78 are imaged onto the detector by the objective 70 in the form of light spots, which are sharp enough to, for example, taking into account an association rule of the type shown in FIG. 3, enable a location in the z direction. The position and extent of the depth of field 78 within the object space are thus predetermined and known.

The device according to FIG. 4 further comprises a control unit 80 which controls the overall operation of the device. In particular, the control unit 80 has computing means which carries out the calculations and evaluations that are necessary to locate the point objects. The control unit 80 further controls a piezoelectric actuator 82, with which the objective 70 can be moved along the optical axis O, in order to shift the depth of field to 78 in a defined manner along the optical axis O. A sensor 84 coupled to the control unit 80 detects the displacement, by which the objective 70, and thus the depth of field 78 are shifted within the object space.

The sample 76 contains various structures 90, 92, 94, 96 and 98, which are arranged in the depth of field 78 in different z positions. The structures 90, 92, 94, 96 and 98 are associated with markers, which form the point objects to be located. During recording, the markers that are located in the structures 90, 92, 94, 96 and 98, are imaged individually as light spots onto the detector and the light spots are evaluated by the control unit 80 with regard to their position and form. A high-resolution image in the z-direction is generated in this manner.

Figure 5:
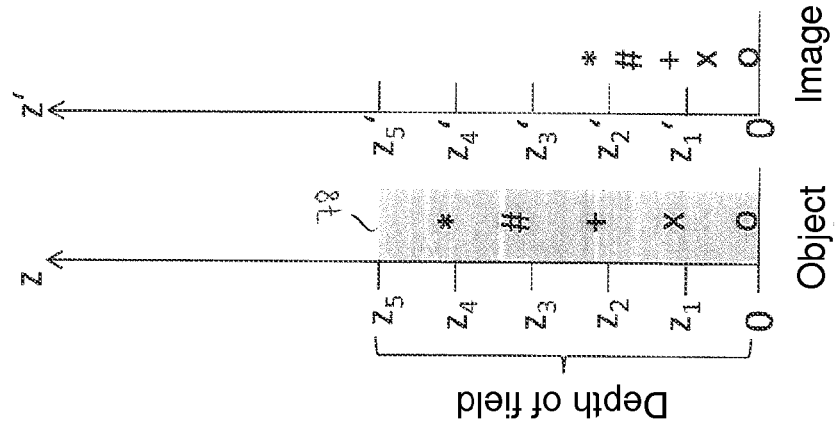
FIG. 5 is a schematic representation illustrating distortion of the sample image in the z direction caused by a faulty association information.

FIG. 5 is a representation in which it is illustrated how a faulty association rule leads to a distortion of the image in the z direction. Thus, the object space with the depth of field 78 is represented in the left part of FIG. 5, in which the structures 90, 92, 94, 96 and 98 are arranged, while the imaging of these structures in the image space is illustrated in the right part of FIG. 5. The z positions within the image space corresponding to the z positions of the object space are characterized with the symbol .'..

In the example according to FIG. 5, the faulty association rule leads to a compression of the image in the z' direction.

In FIG. 6 it is represented how this compression of the image caused by the faulty association rule is successively eliminated in that the depth of field 78 is shifted in the z direction in several steps. The partial image a) of FIG. 6 thereby corresponds to the situation represented in FIG. 5.

First, a z reference position is defined in the depth of field 78, which position is stationary relative to the depth of field 78, that is, is shifted together with the depth of field 78 in the object space. In the present example, the lower limit of the depth of field 78 designated as $z_s$ is set as the reference position z. Since this z reference position is known, the z position of the structure within the sample, which is located in the z reference position, can be detected accurately and without errors. In the partial image a) of FIG. 6, in which the depth of field 78 has not yet been shifted, this applies to the structure 90.

If the sample is now imaged onto the detector and then the depth of field 78 is moved together with its z reference position to the position $z_s=z_1$, the situation represented in the partial image b) of FIG. 6 results. There, the structure 92 is in the z reference position of the depth of field 78. The z position can now be determined accurately for the point objects that are contained in the structure 92 arranged in the z reference position. The light spots which are generated on the detector from the point objects arranged in the z reference position, are hereinafter referred to as reference light spots. By means of these reference light spots light spots are now identified in the previously recorded first sample image (partial image a of FIG. 6), which correspond to the reference light spots of the second sample recorded with the shifted depth of field 78. These light spots contained in the first sample image are designated as comparison light spots in the following.

As a comparison of partial images a) and b) of FIG. 6 shows, the z position of the point objects contained in the structure 92 has been determined wrongly due to the faulty association rule, namely with a value $z_x'$ which is too small. This wrong value can now be replaced by the value correctly determined in the second sample image and thus be corrected. This correct value is known as $z_1=z_1'$.

As shown in FIG. 7, the correct position $z_1$ of the structure 92 can now be plotted against the faulty position $z_x'$ in a graph, namely the position that has been found for the structure 92 in the first sample image partial image a).

Now the depth of field 78 is again moved by a defined displacement, which is smaller than the axial extent t of the depth of field 78. In this example, the displacement provided in the second shifting step is again equal to the amount $D_z$, so that the z reference position is shifted into the position $z_2$. A sample image is recorded again and the structure is considered again, which is arranged in the z reference position, that is, at the lower limit of the depth of field 78. According to the partial image c) of FIG. 6, this is presently the structure 94, whose point objects generate the associated reference spots on the detector. By means of these reference light spots, the associated comparison light spots are again identified in the first sample image (partial image a of FIG. 6) identified, that is, the structure 94 is searched for in the first sample image. In the first sample image, the z position $z_+'$ is assigned to the structure 94. In the graph according to FIG. 7, the correct position $z_2$ is plotted against this position $z_+'$.

In the manner described above, it is proceeded in a suitable number of steps, as indicated in FIG. 6 by the partial images d) and e), until the entire original depth of field shown in the partial image a) of FIG. 6, is covered.

For all the structures that have been found again in the first sample image, the correct position can now be read on the ordinate by means of the graph of FIG. 7. On the basis of the represented measurement points, a correction rule can be obtained with the aid of a suitable model function, which takes typical calibration errors into account. Optionally, a simple spline interpolation or an interpolation of another type can also be used to obtain the correction rule.

This correction procedure, which is designated as c (z') in FIG. 7, can now be used to correct the first sample image (partial image of FIG. 6). Thus, the respective correct z position is obtained from the correction rule c(Z') for all positions z' determined from the first sample image.

It should be noted that the above-described method is to be understood as merely exemplary. Other algorithms than the described algorithm can of course be used. In particular, it is skillful with the practical implementation, to not only define one stationary z reference position within the depth of field, as is the case in the example shown in FIGS. 4 to 7. Thus, further z reference positions can be defined in other locations of the depth of field.

It is also feasible to not only consider the deviations of the nth image with regard to the first sample image, but also to determine position deviations of structures from the nth image with regard to structures from the mth image, wherein n and m are natural numbers equal or greater than 1. This results in more measurement points, so that a more precise correction rule can be determined. Image processing algorithms can also be used, which directly determine the distortions of the nth image compared to the structures also occurring in the mth image. It is only essential that an additional information regarding the z position of the considered structure is present via a highly exact shifting of the depth of field, which is used skillfully for locating the point objects.

Also, the value regions of z or z', that is the depth of field and the corresponding image region, can be adapted flexibly if the correction rule cannot be applied to the respective entire sample region.

Furthermore, it is also possible to use the position information gained with the shifted depth of field not only for the correction of the z positions determined in the first sample image, but to let this position information flow into the image generation itself.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A light-microscopy method for locating point objects in a sample arranged in an object space, the sample being imaged onto a detector by an imaging optical unit having a depth of field of predetermined axial extent along an optical axis in the object space, onto which the detector is imaged, wherein the point objects in the sample are located within the depth of field, wherein a first sample image generated by the imaging of the sample onto the detector is evaluated, wherein, for locating a respective first point object in a direction of the optical axis, a parameter of a first light spot of one or more light spots of the first sample image representing the first point object is determined, and a first axial z position related to the first point object is assigned to the parameter based on predetermined association information, the method comprising:

shifting the depth of field within which the point objects are located in the object space relative to the sample along the optical axis by a predetermined axial displacement, the predetermined axial displacement being smaller than the predetermined axial extent of the depth of field;

imaging, by the imaging optical unit, the sample onto the detector with the axially shifted depth of field to generate at least a second sample image;

determining second image z positions of the point objects in the second sample image based on the predetermined axial displacement;

comparing first image z positions of the point objects in the first sample image to the second image z positions of the point objects in the second sample image; and generating, based on the comparing the first image z positions of the point objects in the first sample image to the second image z positions of the point objects in the second sample image, correction information so as to correct the first axial z position related to the first point objects based on the predetermined association information.

2. The light-microscopy method according to claim 1, wherein at least one z reference position, which is stationary relative to the depth of field, is defined within the depth of field along the optical axis, the method further comprising:

defining, from one or more light spots from the second sample image that represent the point objects arranged in the axially shifted depth of field in the z reference position, a reference light spot that represents a reference point object determining the z position of the reference point object in the object space based on the axial displacement of the depth of field and the z reference position; and identifying one of the one or more light spots from the first sample image as a comparison light spot, wherein the comparison light spot represents, in the first sample image, the reference point object, wherein generating, based on the comparing the first image z positions of the point objects in the first sample image to the second image z positions of the point objects in the second sample image, correction information for correcting the first axial z position related to the first point object based on the predetermined association information comprises generating, based on a deviation of the z position of the reference point object as represented by the comparison light spot and the z-position of the reference point object as represented by the reference light spot, the correction information.

3. The light-microscopy method according to claim 2, wherein the depth of field is axially shifted in several steps, wherein in each of these steps, the correction information is generated based on the respective reference light spot and the corresponding comparison light spot, and wherein the z positions of the point objects determined in dependence on the association function are corrected by means of the gradually generated correction information.

4. The light-microscopy method according to claim 3, wherein the z position determined for the respective comparison light spot based on the association information is replaced in each step by the z position determined for the corresponding reference light spot, and that a correction function as correction information is generated by this replacement.

5. The light-microscopy method according to claim 4, wherein intermediate values of the correction function, for which no comparison light spots and reference light spots are available by the gradual shift of the depth of field, are determined by interpolation.

6. The light-microscopy method according to claim 3, wherein the z positions of the point objects determined by gradually shifting the depth of field are superimposed to a total locating image.

7. The light-microscopy method according to claim 2, wherein a comparison structure of the comparison light spots formed by the comparison light spots is identified while considering its brightness.

8. The light-microscopy method according to claim 3, wherein the sum of the individual axial displacements is substantially equal to the axial extent of the depth of field.

9. The light-microscopy method according to claim 1, wherein the axial displacement is detected by a sensor.

10. The light-microscopy method according to claim 1, wherein the depth of field in the object space is shifted relative to the sample along the optical axis by the axial displacement by shifting the sample relative to the imaging optical unit or by shifting the imaging optical unit relative to the sample along the optical axis.

11. The light-microscopy method according to claim 1, wherein the predetermined association information is obtained by moving a calibration point object within the depth of field along the optical axis and detecting the parameter of the first light spot representing a calibration point object of a calibration image generated on the detector in dependence on a z position of the calibration point object.

12. The light-microscopy method according to claim 1, wherein an arrangement with two detection channels is used as a detector, wherein a first detection channel having a first image plane optically conjugated to be a first focal plane, and wherein a second detection channel has a second image plane offset along the optical axis with regard to the first image plane, which is optically conjugated to a second focal plane offset along the optical axis with regard to the first focal plane.

13. The light-microscopy method according to claim 1, further comprising:

using a cylindrical lens upstream of the detector, which leads to a distinguishable change in form of the light spot generated on the detector, when a point object assigned to one of the one or more light spots along the optical axis is moved from one side to another side of a focal plane lying in the depth of field.

14. The light-microscopy method according to claim 1, wherein one of a form or an extent of the first light spot is used as the parameter.

15. A light-microscopy device for locating point objects in a sample, the light-microscopy device comprising
- an imaging optical unit having a depth of field of a predetermined axial extent along its optical axis in an object space;
- a detector, onto which the imaging optical unit can image a sample arranged in the object space; and
- a control unit operable to locates one or more point objects contained in the sample within the depth of field, the control unit being operable to evaluate a first sample image that the imaging optical unit generates on the detector;
- wherein the control unit is operable to determine a parameter of a first light spot of the first sample image, the first light spot representing a first point object of the one or more point objects contained in the sample and to assign an axial z position to the parameter based on predetermined association information;
- wherein the control unit is further operable to control a driven adjustment unit to shift the depth of field within which the point objects are located in the object space relative to the sample along the optical axis about a predetermined axial displacement which is the smaller than the axial extent of the depth of field;
- wherein the imaging optical unit is operable to generate a second sample image by imaging the sample onto the detector with an axially displaced depth of field;
- wherein the control unit is operable to determine z-positions of the point objects in the second sample image based on the predetermined axial displacement;
- wherein the control unit is operable to compare the z positions of the point objects determined in the first sample image with the z positions of the point objects determined in the second sample image; and
- wherein the control unit is operable to generate correction information based on the comparison of the z positions of the point objects determined in the first sample image with the z positions of the point objects determined in the second sample image, so as to correct the z positions of the point objects determined in dependence on the association information.

16. The light-microscopy device according to claim 15, wherein the control unit is operable to define at least one stationary z reference position in the depth of field along the optical axis;
- wherein the control unit is operable to define at least one of one or more light spots from the second sample image as a reference light spot;
- wherein the control unit is operable to determine a reference z-position of a reference point object represented by the reference light spot based on the axial displacement of the depth of field and the z reference position;
- wherein the control unit is operable to identify one of the one or more light spots from the first sample image as a comparison light spot, wherein the comparison light spot represents the reference point object; and
- wherein the control unit is operable to generate the correction information based on a deviation of the z-position represented by the comparison light spot and the z position represented by the reference light spot.

17. The light-microscopy device according to claim 15, further comprising a sensor for detecting the axial displacement of the depth of field.

* * * * *